United States Patent [19]

Hartmann et al.

[11] 4,102,648
[45] Jul. 25, 1978

[54] MEASURING NON-METHANE HYDROCARBON CONTENTS IN GASES

[75] Inventors: Karl Hartmann, Schöneck; Wolfgang Treis, Bad Soden, am Taunus, both of Fed. Rep. of Germany

[73] Assignee: Hartmann & Brawn Aktiengesellschaft, Frankfurt, Fed. Rep. of Germany

[21] Appl. No.: 806,773

[22] Filed: Jun. 15, 1977

[30] Foreign Application Priority Data

Jun. 16, 1976 [DE] Fed. Rep. of Germany ....... 2626905

[51] Int. Cl.² ..................... G01N 31/10; G01N 31/12; B01D 53/16
[52] U.S. Cl. ............................. 23/254 EF; 23/232 E; 23/254 E
[58] Field of Search ............. 23/232 R, 232 E, 254 R, 23/254 E, 255 R, 255 E, 254 EF; 73/23, 23.1; 134/19

[56] References Cited

U.S. PATENT DOCUMENTS 4,042,332  8/1977  Saitoh et al. .................... 23/232 EX

*Primary Examiner*—R. E. Serwin
*Attorney, Agent, or Firm*—Ralf H. Siegemund

[57] ABSTRACT

The sample gas is divided into two portions, one being subjected to flame ionization detection to measure all hydrocarbons, the other one being passed through a tube having active carbon to remove all higher hydrocarbons by adsorption except methane. The resulting gas is also subjected to flame ionization detection and the difference in detection gives the non-methane impurities, either electrically as difference signal or graphically. The adsorber tube may be exchanged for another one while the former is cleaned and purged. A simple flame ionization detector is used alternatingly or two are operated in parallel to obtain the two readings.

5 Claims, 3 Drawing Figures

MEASURING NON-METHANE HYDROCARBON CONTENTS IN GASES

BACKGROUND OF THE INVENTION

The present invention relates to measuring the content of hydrocarbons in gases, and more particularly the present invention relates to measuring the methane-free portion in the hydrocarbon content in gases, such as exhaust fumes, using at least one flame ionization detector.

Flame ionization detectors, in the following simply referred to as FID's, are used for quite a long time as instruments for measuring the hydrocarbon content in gases. These known instruments operate per se without discriminating as far as methane is concerned. Exhaust and emission measurements which are being undertaken at the present time and to an increasing degree for purposes of improving ecology and the environment, have shown that the inherently included methane content influences the measurement to such an extent that measuring the total content in hydrocarbon is really of very little informative value because the methane content is usually comparatively large but methane is not a gas or component which contributes to the contamination of the environment. Also, whenever measurements of exhaust emission of a combustion engine are undertaken, it was found that the exhaust gases contain a significant quantity in methane. Moreover that methane content varies greatly as it depends on the type of engine, on the fuel used, on the operation of conditions generally and also on the equipment destined to remove contaminants. It was found, for example, that the methane content in the exhaust gases may be as high as about 45%. Since the content in methane varies to a large degree, an integrated measurement really may depict to a considerable extent the variation in methane and, therefore, does not yield adequate information on true contamination. Therefore, the development and construction of combustion engines requires a more discriminating knowledge about the hydrocarbon content, and particularly it is necessary to learn more about the non-methane portion of the hydrocarbons.

The German Petty Patent No. 7403841 discloses a device for the methane-free measurement of hydrocarbon concentration in a gas by means of two FID's. They are constructed to receive two streams of sample gas whereby one of the gases contains all hydrocarbons, and the second stream contains only methane and a difference in measuring signals corresponding two of these hydrocarbon contents is formed in order to ascertain the non-methane protion in the hydrocarbon content. In this particular instance, the first FID has a flow delaying chamber disposed ahead of its gas inflow and a chamber containing a catalyst is disposed in the inflow path of the second FID. All higher hydrocarbons of the respective gas sample are combusted in that catalytic chamber, except the methane. The system uses as oxidizer the oxygen content in the respective sample gas. The catalyst is a copper oxide compound. It was found, however, that this particular device offers difficulties concerning the separation by the catalyst of the methane and the other hydrocarbons. Moreover, the catalyst becomes increasingly useless and the metal tube containing the catalyst must be exchanged accordingly. This amounts to an interruption in the measuring process.

DESCRIPTION OF THE INVENTION

It is an object of the present invention to provide a new and improved method and equipment for detecting the non-methane portion among the hydrocarbons in a gas.

In accordance with the preferred embodiment of the present invention it is suggested to use an adsorbing device for removing all hydrocarbons from a portion of the sample gas except methane and to subject the result to flame ionization detection. The resulting output is compared with an output resulting from flame ionization detection of the gas with all hydrocarbons in it. One will use preferably active carbon as adsorbant. In furtherance of the invention a single flame ionization detector is used and alternatingly charged with the unmodified gas as well as with gas that has passed through the adsorbing device to obtain alternatingly the detection signals representing total hydrocarbon content and methane. The difference may be formed through observation of the two readings individually, or an electrical signal of one detector may be stored until a signal for the other measurement is provided, and a differential amplifier establishes the desired difference signal. Alternatively, but of course more expensive, is the use of two flame ionization detectors, both of them being continuously charged with sample gas whereby one flame ionization detector receives the unmodified sample gas and the other one receives the sample gas which has passed through the adsorber and contains methane only. In addition, it may be advisable particularly in those cases when a true continuous reading is required to provide two adsorbing devices and to switch between them back and forth while the respective other one is being cleansed and purged.

It was found that the use of an adsorbing device particularly a tube filled with active carbon, permits an almost complete elimination of the non-methane hydrocarbons from a sample portion so that the outflow of the tube is, in fact, a gas containing methane only as an additive. Even with automatic regeneration being included, the equipment is still quite inexpensive and requires relatively little maintenance.

DESCRIPTION OF THE DRAWING

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding now to the detailed description of the drawings, FIG. 1 illustrates an inlet tube 1 or conduit for a gas sample. The gas sample contains hydrocarbon in general, and the equipment shown is designed to detect the non-methane portion of the hydrocarbon content in the gas. A magnetic valve 2 permits alternatingly feeding of the sample gas into a tubular adsorption chamber 3 (inlet tube 3a), or into a bypass conduit 11. The tube or chamber 3 is filled with active carbon as an adsorbing agent. It was found that active carbon separates to a sufficient degree other hydrocarbons from methane.

Figure 1:
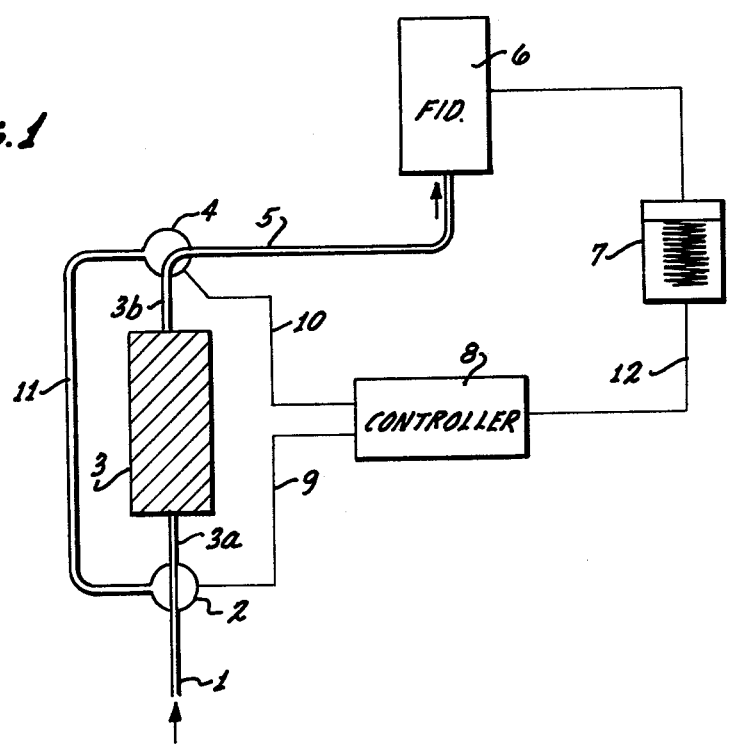
FIG. 1 is a schematic view and block diagram of a first example in accordance with the preferred embodiment of the invention using a single flame ionization detector.

The gas stream leaving the tube 3 through conduit 3b is free from higher valued hydrocarbons and contains practically exclusively the methane content of the sample gas. Tube 3b is connected to a second magnetic valve 4 which alternatingly connect the conduit 3b and the bypass 11 to a duct or conduit 5. Conduit 5 is the inlet tube or duct for a flame ionization detector 6 which, as such, is of known construction. The methane content of the sample gas is detected by itself, whenever the magnetic valves 2 and 4 have the illustrated position so that conduit 5 feeds the sample gas minus the higher valued hydrocarbons into the flame ionization detector 6. This detector 6 operates in a conventional manner and drives, for example, a recording device or plotter 7, recording the methane content accordingly.

Reference numeral 8 refers to a program controller which, in effect, alternates the valve position. Upon changing the positions of valves 2 and 4 from the illustrated position into the alternative positions, the conduit 5 is directly connected to conduit 1 via the bypass 11. In this case the flame ionization detector 6 receives the sample gas with all its hydrocarbons in it. The change in that position may also be signalled by the controller 8 to the recorder 7 via the line 12 to turn on a second recording channel to separately record the total hydrocarbon content as now detected by the flame ionization detector 6.

As stated, program device and controller 8 alternates the position of the valves 2 and 4 and accordingly the recorder 7 records a sequence of signals representing alternately the methane control and the total hydrocarbon content. The difference in these readings represents the content of hydrocarbon in the sample gas other than methane and, therefore, that difference represents the true contamination. The device shown in FIG. 1 is of a comparatively simple nature and has the disadvantage that the tube or chamber 3 has to be replaced from time to time because the adsorbing agent becomes sooner or later saturated and loses its adsorbing effect. This disadvantage is avoided in the improved device shown in FIG. 2. It should be noted that FIG. 2 includes two modifications; either can be practiced without the other as a modification of FIG. 1.

Figure 2:
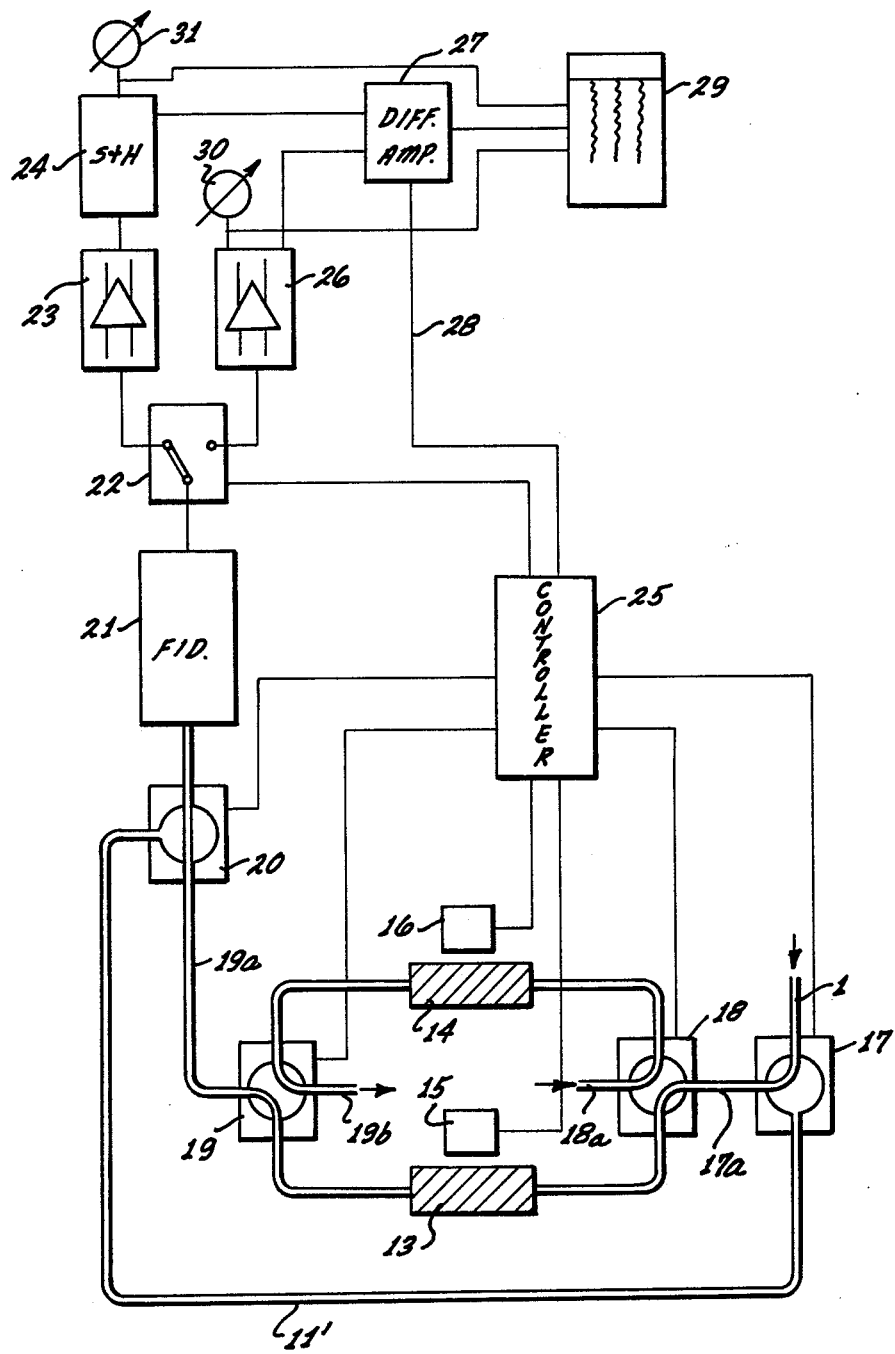
FIG. 2 is analogously a block diagram showing a second example of the preferred embodiment which includes a single FID and exchangeable adsorption equipment.

In the particular device shown in FIG. 2 the sample gases are again fed through a conduit 1 but in this case conduit 1 is connected to a three way valve 17 which runs the gas flow either into the bypass 11' or into a conduit 17a. A four way valve 18 will guide the flow to a first adsorbing tube 13. The gas containing pure methane and no other hydrocarbons and flowing out of tube 13 runs through another four way valve 19 to a three way valve 20 which in turn feeds a flame ionization detector 21.

Just as in FIG. 1 this FID 21 could be connected to drive a plotter 7. However one of the modifications shown in FIG. 2 involves the output device of the single FID as used. The electrical output FID 21 is connected via a switch 22, for example, to a peak amplitude amplifier 23 which feeds its output to a storage facility 24, such as a sample and hold circuit.

For measuring the total hydrocarbon content a control and program device 25 operates the valves 17 and 20 to assume the alternative position whereupon sample gas conduit 1 is connected via the by-pass 11' to the input of the flame ionization detector 21. In addition, program device 25 places switch 22 into the alternative position and the electrical output of the flame ionization detector 21 is now connected to am amplifier 26. The output of amplifier 26 is indicative of the entire hydrocarbon content.

Reference numeral 27 refers to a differential amplifier i.e. to a difference forming circuit generally, which compares the signal stored in device 24 (methane content) with the current signal provided by the amplifier 26 (all hydrocarbons). The output of the differential amplifier 27 is in effect a direct indication of the non-methane portion in the hydrocarbon content of the sample gas. The output signal of differential amplifier 27 is fed to the recorder 29 which in this case will record, at least in one channel, just the desired contaminating components. The methane content as derivable from amplifier 23 or store 24 can be separately recorded and, possibly, indicated in an instrument 31. Analogously, the total hydrocarbon content can be recorded in still another channel, and the output of amplifier 26 may also be separately indicated by an instrument 26.

The program device 25 operates the valves 17 and 19 just as programmer 8 controls valves 2 and 4, in alternating sequence whereby, however, device 25 alternates additionally the position of switch 22 in synchronization with the valve changes. In addition, programmer 25 operates the two valves 18 and 19 to thereby eliminate the adsorbing tube 13 from the sample gas path and instead a second adsorbing tube 14 is interconnected between the conduit 17a and 19a. The measurement now proceeds with the aid of adsorbing tube 14. This position change of valves 18, 19 may be synchronized with a position change of valves 17, 20, so that the equipment does not "see" this change in adsorber tube.

The now separated tube 13 is heated by heater 15 acting also under control of device 25 and is flushed through separately by a hydrocarbon cleansing gas applied to the system via a conduit 18a and discharged via a conduit 19b. This way the previously adsorbed hydrocarbons will be purged and removed from the heated tube 13 whereby in principal the cleansing action may last as long as the tube 14 is used as adsorber for the non-methane hydrocarbons.

The programmer 25 alternates occasionally the connections for the tubes 13 and 14. As one of the adsorbing tubes is cleaned and refreshed, the other one is being used and vice versa. This way, no interruption is incurred on account of saturating the adsorbing agent with the material it adsorbs. Tube 14 has its own heater 16. Actually, in the illustrated position of the values tube 14 is purged and refreshed under heating by 16, while tube 13 works as adsorber. Finally, it should be mentioned that the purging and refreshing system as shown in FIG. 2 could be used as a modification of FIG. 1 independent from the modification in the electrical and read-out portion of the system.

Figure 3:
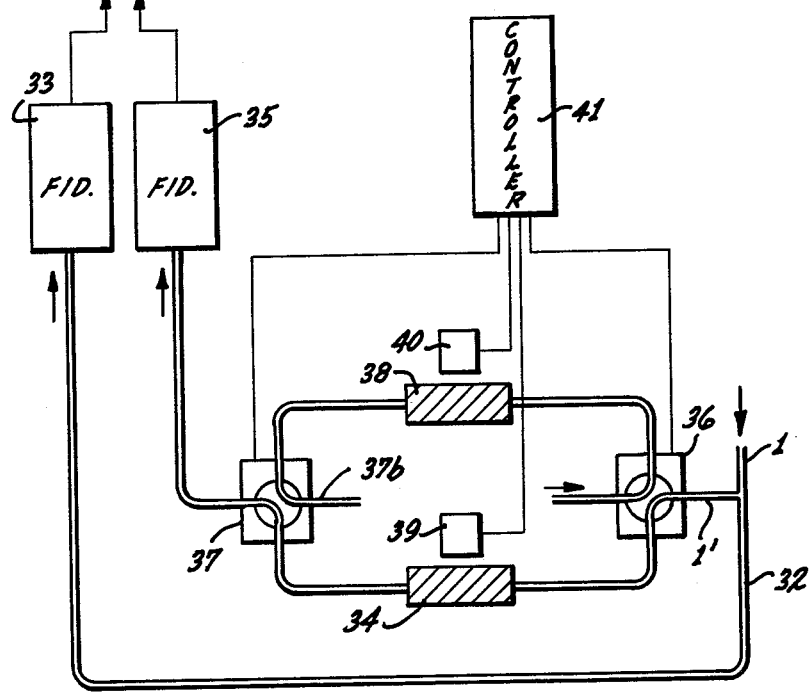
FIG. 3 is a block diagram of a system using two FID's and exchangeable adsorption equipment.

Proceeding now the the description of the example shown in FIG. 3, this equipment provides for an almost continuous measurement of the methane and of the non-methane hydrocarbon content in the sample gas. In this particular case, there is a continuous connection of the input pipe 1 to a first flame ionization detector 33, the conduit connection being identified by reference numeral 32. A second connection or a branch pipe 1' leads either to an adsorbing tube 34 or to an adsorbing tube 38, depending upon the position of the four-way valve 36 which is similar to valve 18 in FIG. 2. Valve 36 feeds also cleansing gas, i.e. hydrocarbon free gas from an inlet 36a to an adsorbing tube 38 which is presently not connected to conduit 1. Analogously, a second valve 37 being constructed and positioned similar to the valve 19 in FIG. 2 feeds either the output of tube 34 containing exclusively gas plus methane to a second flame ionization detector 35 while simultaneously the cleansing gas extracted from the respective other adsorbing tube, e.g. 38 is fed to the outlet conduit 37b for discharge of the purging and cleansing agent.

A change in position of the valves 36 and 37, particularly from the illustrated position, will connect the tube between sample gas line 1 and 38 FID 35, while tube 34 is purged by cleansing gas. Reference numerals 39 and 40 respectively refer to the two heaters for the two adsorbing 34 and 38. A controller and program device 41 operates the valves 36, 37 as well as the heaters 39 and 40 in a manner similar to the operation of programmer 25 described with reference to FIG. 2.

The two FID 33 and 35 therefore, receive respectively continuously gas with the full hydrocarbon content and gas containing methane only, and the electrical output signals provided by the FID's 33 and 35 are analogously fed to a differential amplifier 42. The output of the amplifier 42 is connected to a recorder 43 to record the resulting measurement of which is indicative of the methane free, hydrocarbon contamination of the gas. It should be mentioned that also here the individual components such as the total hydrocarbon content and the methane content may be recorded separately, if such information is of interest to the user.

This particular example employs two individual flame ionization detectors, they are described as individual conventional units. However, an integrated device can be employed using common components which can be shared, such as a simple housing but with two burner chambers. Also it was mentioned above that FIG. 3 illustrates a quasiconcurrent measuring device. Actually, one could speak of true concurrency here, the only deviation from continuous concurrency occurs upon those infrequent instances in which one switches over from one adsorbing tube to the other one which in fact amounts to a very brief interruption only in the measurement.

Another modification and simplification should be mentioned; the various valves do not have to be operated automatically by program and control devices. Instead one may operate them manually as far as timing is concerned whereby the various valves should still have interconnected energizing circuits because each pair of valves, 2 and 4, 17 and 20, 18 and 19, 36 and 37, should be actuated in unison.

The invention is not limited to the embodiment described above but all changes and modifications thereof not constituting departures from the spirit and scope of the invention are intended to be included.

We claim:

1. Apparatus for measuring the non-methane portion in the hydrocarbon content of gases comprising:

an unheated adsorbing device containing uncoated, active carbon and receiving a portion or sample of said gas, the carbon being exposed to the gas for removing the hydrocarbons therefrom, except the methane by adsorbing these hydrocarbons;

flame ionization means for measuring the total hydrocarbon content in said sample gas and for separately measuring said sample gas having passed through said adsorbing device to obtain a representation of the methane content only in the carbon gas; and means for obtaining an indication of the measuring signals as provided by said flame ionization means from which to obtain an indication of the non-methane hydrocarbon content in said sample gas.

2. Apparatus as in claim 1 wherein said flame ionization detection means is a single flame ionization detector alternately charged with the unmodified sample gas as well as with an output of said adsorbing device to thereby provide alternatingly two signals that represent the total hydrocarbon content as well as the methane content.

3. Apparatus as in claim 2 including temporary signal storage means connected to said flame ionization detector and difference forming means connected to the storage means as well as to the flame ionization detector to form the difference between said two signals in representation of the non-methane portion of the hydrocarbon content of said sample gas.

4. Apparatus as in claim 1 including a second adsorbing device and means for alternating feeding sample gas to said first mentioned adsorbing device and to said second adsorbing device; and cleaning and purging means for connection to the respective other one of said two adsorbing devices when not receiving said sample gas.

5. Apparatus as in claim 1, including means for heating the adsorbing device, being inactive during said measurement, and means passing a flow of cleansing gas through the adsorbing device while the device is heated by the means for heating, to remove adsorbed material from the carbon, said adsorbing device being disconnected from a source of sample gas during the cleaning.

* * * * *

UNITED STATES PATENT AND TRADEMARK OFFICE
CERTIFICATE OF CORRECTION

PATENT NO. : 4,102,648
DATED : July 25, 1978
INVENTOR(S) : Karl Hartmann, et al

It is certified that error appears in the above-identified patent and that said Letters Patent are hereby corrected as shown below:

[75] KARL HARTMANN, Schöneck; WOLFGANG TREIS, Bad Soden/Taunus; both of the Fed. Rep. of Germany Signed and Sealed this Thirteenth Day of March 1979

[SEAL]

Attest:

RUTH C. MASON
Attesting Officer

DONALD W. BANNER
Commissioner of Patents and Trademarks